United States Patent
Brandon et al.

(10) Patent No.: US 9,442,093 B2
(45) Date of Patent: Sep. 13, 2016

(54) TIRE METALLIC CABLE ANOMALY DETECTION METHOD AND APPARATUS

(75) Inventors: Lee Brandon, Piedmont, SC (US); Gene Edward DeAmicis, Nayaril (MX); Frank E. Gramling, Simpsonville, SC (US); David Andrew Judd, Mauldin, SC (US)

(73) Assignees: MICHELIN RECHERCHE et TECHNIQUES S.A., Granges-Paccot (CH); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 113 days.

(21) Appl. No.: 13/260,744

(22) PCT Filed: Mar. 31, 2010

(86) PCT No.: PCT/US2010/029390
§ 371 (c)(1),
(2), (4) Date: Sep. 28, 2011

(87) PCT Pub. No.: WO2010/117855
PCT Pub. Date: Oct. 14, 2010

(65) Prior Publication Data
US 2012/0038357 A1    Feb. 16, 2012

(30) Foreign Application Priority Data
Apr. 9, 2009 (WO) ................ PCT/US2009/040017

(51) Int. Cl.
*G01R 33/06* (2006.01)
*G01N 27/82* (2006.01)

(52) U.S. Cl.
CPC ..................................... *G01N 27/82* (2013.01)

(58) Field of Classification Search
CPC ...... G01N 27/82; G01N 27/90; G01N 27/72; G01M 17/02; G01M 17/022; G01R 33/06; G01R 33/02; B29D 30/06; B29D 2030/0077

USPC .......... 324/225–251, 325–351; 73/146, 582, 73/588; 209/538, 567
See application file for complete search history.

(56) References Cited

U.S. PATENT DOCUMENTS

| 2,345,679 A | 4/1944 | Linse |
| 3,604,249 A | 9/1971 | Wilson |

(Continued)

FOREIGN PATENT DOCUMENTS

| CN | 101266226 A | 9/2008 |
| EP | 514162 A1 | 11/1992 |

(Continued)

OTHER PUBLICATIONS

PCT International Search Report for PCT/US2010/029390, dated Jun. 3, 2010.

(Continued)

*Primary Examiner* — Son Le
*Assistant Examiner* — Brent J Andrews
(74) *Attorney, Agent, or Firm* — Dority & Manning, P.A.

(57) ABSTRACT

Disclosed is an apparatus and methodology for detecting anomalies in cables within a tire structure. A plurality of magnetic field sensitive sensors are aligned within a magnetic field provided by a magnet. The alignment of sensors and magnet is such that flux lines from the magnet are generally parallel to the plane occupied by the magnetic sensors. A tire cable anomaly present between the magnetic field sensitive sensors produces a detectable difference in signals produced by the magnetic field sensitive sensors as a result of the formation of perpendicular flux patterns produced by the anomaly. A signal processing circuit receiving input signals from the sensors evaluates differences between the signals from each of the plurality of sensors by pairing the output signal from each sensor with the output signal from each of the others of the plurality of sensors and produces an output signal upon the differences meeting selected criteria. The output signal may include an externally measurable signal and/or may include a visual signal indicating presence of a tire anomaly.

14 Claims, 8 Drawing Sheets

(56) References Cited

U.S. PATENT DOCUMENTS

| | | |
|---|---|---|
| 3,815,407 A | 6/1974 | Lavery |
| 4,285,235 A | 8/1981 | Dugger |
| 4,538,108 A * | 8/1985 | Huschelrath .......... G01N 27/82 324/232 |
| 4,659,991 A | 4/1987 | Weischedel |
| 4,785,354 A | 11/1988 | Nakamura et al. |
| 5,060,136 A | 10/1991 | Furney et al. |
| 5,060,250 A | 10/1991 | Kwee et al. |
| 5,402,685 A | 4/1995 | Brobeil |
| 5,548,214 A * | 8/1996 | Yasohama .......... G01N 27/9086 324/228 |
| 5,559,437 A | 9/1996 | Baccaud et al. |
| 5,565,771 A * | 10/1996 | Hamelin et al. ............... 324/225 |
| 5,804,964 A * | 9/1998 | Hamelin et al. ............... 324/242 |
| 6,005,388 A * | 12/1999 | Kaefer-Hoffmann et al. .......................... 324/240 |
| 6,050,173 A | 4/2000 | Sakai et al. |
| 6,539,789 B1 | 4/2003 | Kostka et al. |
| 6,600,326 B2 | 7/2003 | Weiss |
| 7,082,819 B2 | 8/2006 | Thiesen et al. |
| 7,095,963 B2 | 8/2006 | Knaack et al. |
| 7,185,534 B2 | 3/2007 | Stoila et al. |
| 7,185,535 B2 | 3/2007 | Beckley et al. |
| RE40,166 E | 3/2008 | Sukhorukov et al. |
| 7,411,391 B2 | 8/2008 | Desplats |
| 7,416,624 B2 | 8/2008 | Stoila et al. |
| 2005/0229690 A1 | 10/2005 | Kikuchi et al. |
| 2007/0029027 A1* | 2/2007 | Stoila et al. ............... 156/110.1 |

FOREIGN PATENT DOCUMENTS

| | | |
|---|---|---|
| EP | 580024 A1 | 1/1994 |
| EP | 681181 A1 | 11/1995 |
| FR | 2433178 A1 | 7/1979 |
| GB | 2071331 A | 9/1981 |
| GB | 2203549 A | 10/1988 |
| GB | 2324155 A | 10/1998 |
| JP | 52078283 A | 7/1977 |
| JP | 59039538 B | 3/1984 |
| JP | S 59217158 A | 12/1984 |
| JP | 1154735 A | 6/1989 |
| JP | A-H06-160354 | 6/1994 |
| JP | 7253448 A | 10/1995 |
| JP | A-H09-188496 | 7/1997 |
| JP | A-H11-248684 | 9/1999 |
| JP | A-2006-10440 | 1/2006 |
| JP | 2008309643 A | 12/2008 |
| JP | 2008309644 A | 12/2008 |
| JP | 2008309646 A | 12/2008 |
| WO | WO 2006/067361 A1 | 6/2006 |

OTHER PUBLICATIONS

European Search Report dated Apr. 20, 2015. 7 pages.

* cited by examiner

HE1  　706  　HE2
702  　　　　704

TIRE METALLIC CABLE ANOMALY DETECTION METHOD AND APPARATUS

CROSS REFERENCE TO RELATED APPLICATIONS

This application claims benefit of PCT Application PCT/US2009/040017, filed on 9 Apr. 2009.

FIELD OF THE INVENTION

The present subject matter relates to tire testing. In particular, the present subject matter relates to methods and apparatus for non destructive testing for the presence of anomalies in metallic cables within a tire.

BACKGROUND OF THE INVENTION

Tire repair including tire retreading is well known in the art. It is also well known that some level of testing of the tire prior to repair including retreading is normally conducted to determine whether it is appropriate to perform the operation. While in some instances testing may include simple visual inspection, it is often important in the case of retreading to determine the condition of internal components of the tire including, for example, sidewall casing wires.

Generally such determinations have been performed using x-ray analysis based upon visual or shearographic image inspection. Frequently shearographic image inspection is actually followed by x-ray inspection to determine if an identified abnormality is cable related. Such methods, however, are time consuming and the required equipment is expensive to own and operate. It would be advantageous, therefore, to develop apparatus and methodologies that eliminate the need for some of these expensive and time consuming methods.

U.S. Pat. No. RE 40,166 to Sukhorukov et al. is directed to a magnetic non-destructive method and an apparatus for measurement of cross sectional area of elongated ferrous objects such as steel wire ropes and for detecting local flaws.

U.S. Pat. No. 4,659,991 to Weischedel is directed to a "Method and apparatus for magnetically inspecting elongated objects for structural defects."

U.S. Pat. No. 5,565,771 to Hamelin et al. is directed to "Apparatus for increasing linear resolution of electromagnetic wire rope testing."

U.S. Pat. No. 5,804,964 to Hamelin et al is directed to a "Wire rope damage index monitoring device."

U.S. Pat. No. 6,005,388 to Kaefer-Hoffmann et al. is directed to a "Device and process for detecting defects in the disposition of reinforcing members of magnetizable material in casing plies in the sidewall region of a tire."

U.S. Pat. No. 7,185,535 to Stoila et al. is directed to a "Ply wire sensor system for a tire."

While various implementations of tire inspection apparatus and methodologies have been developed, and while various combinations of inspection methodologies have been developed, no design has emerged that generally encompasses all of the desired characteristics as hereafter presented in accordance with the subject technology.

SUMMARY OF THE INVENTION

In view of the recognized features encountered in the prior art and addressed by the present subject matter, an improved apparatus and methodology for testing for anomalies in tires has been developed.

In an exemplary configuration, an apparatus for detecting tire metallic cable anomalies is provided comprising a plurality of magnetic field sensors positioned along a common line and configured to produce individual electrical signals proportional to a sensed magnetic field, a magnet having north and south poles thereof positioned to provide a magnetic field at each said plurality of magnetic field sensors parallel to said common line, and a signal processing circuit configured to produce signals indicative of differences between pairs of said individual electrical signals, wherein the electrical signal from each of said plurality of magnetic field sensors is paired with an electrical signal from each of the others of said plurality of magnetic field sensors. In particular embodiments, the plurality of magnetic field sensors comprise surface mount Hall effect sensors.

In accordance with other embodiments of the present subject matter, the signal processing circuit is configured to pair the strongest electrical signal with the strongest opposing electrical signal to produce a damage magnitude signal while ignoring the remaining electrical signals. In accordance with other embodiments of the present subject matter the signal processing circuit is configured to produce a signal based on one of subtractive signal differences, the presence of opposite sloped signals with slopes each exceeding a predetermined magnitude, and convolution analysis of zero averaged multiplied waveforms.

In accordance with further embodiments of the present subject matter, a structure is provided and configured to support the plurality of magnetic field sensors and the magnet to that the plurality of magnetic field sensors may be manually presented to a metallic cable for detection of anomalies therein. In particular further embodiments, an automated control system is provided and configured to automatically present the plurality of magnetic field sensors to a metallic cable for detection of anomalies therein.

In accordance with certain embodiments of the present subject matter at least three magnetic field sensors are provided while in still further embodiments the magnet is a permanent magnet.

The present subject matter also relates to a method for detecting anomalies in a tire metallic cable comprising positioning a plurality of magnetic field sensors on a common line, positioning a magnet having north and south poles thereof to provide a magnetic field at each of the plurality of magnetic field sensors parallel to said common line, presenting the plurality of magnetic field sensors to a metallic cable, and detecting a difference between signals produced by each of the plurality of magnetic field sensors paired with each one of the others of said plurality of magnetic field sensors.

In certain embodiments, the method further comprises pairing the strongest positive signal from each of the plurality of magnetic field sensors with the strongest negative signal from each one of the other magnetic field sensors and analyzing the difference between the strongest positive and strongest negative signals to the exclusion of the remaining magnetic field sensor signals. In certain further embodiments, the method further comprises producing a signal based on one of subtractive signal differences, the presence of opposite sloped signals with slopes each exceeding a predetermined magnitude, and convolution analysis of zero averaged multiplied waveforms.

In certain embodiments of the method of the present subject matter, positioning of the magnetic field sensors comprises positioning surface mount Hall effect sensors and in particular embodiments positioning a magnet comprises positioning both the north and south poles of a magnet along a line parallel to the common line.

In certain particular embodiment of the present subject matter, positioning a plurality of magnetic field sensors comprises positioning at least three magnetic field sensors while in other particular embodiments positioning a magnet comprises positioning a permanent magnet.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
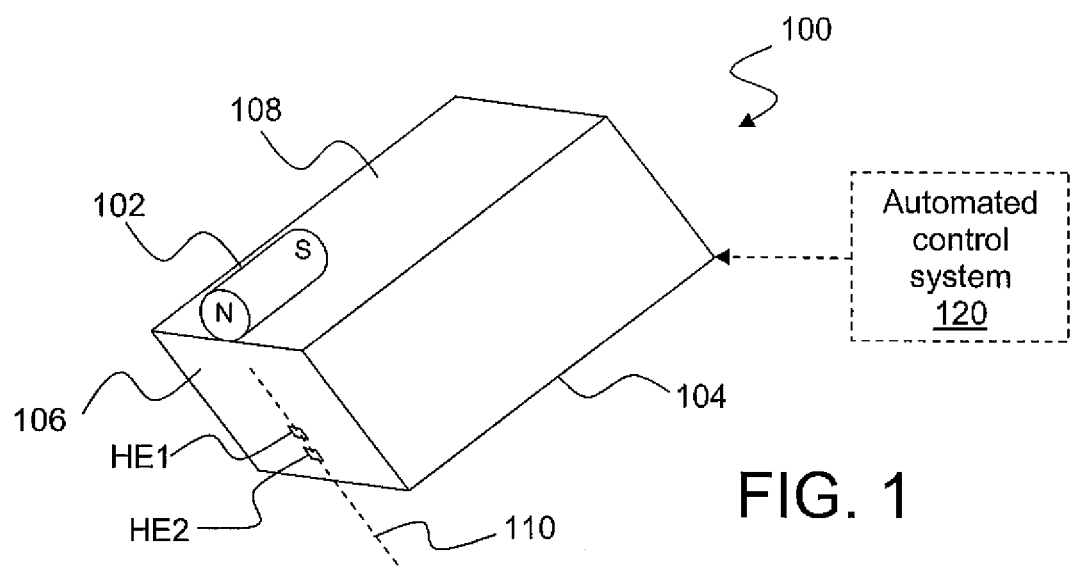
FIG. 1 illustrates an exemplary configuration of a Hall effect and permanent magnet sensor in accordance with present technology including an optional automated control system.

Repeat use of reference characters throughout the present specification and appended drawings is intended to represent same or analogous features or elements of the invention.

DETAILED DESCRIPTION OF THE PREFERRED EMBODIMENTS

As discussed in the Summary of the Invention section, the present subject matter is particularly concerned with improved apparatus and methodology for testing for anomalies in tires, in particular anomalies in metallic cables corresponding to tire cord structure.

It should be appreciated by those of ordinary skill in the art that while the present disclosure is discussed primarily in relation to the detection of anomalies in metallic cables associated with tire structures, such is not a specific limitation of the either the described apparatus or operational methodologies. For example, substantially identical apparatus and methodologies may be applied to the detection of anomalies in magnetically responsive elongated structures associated with or embedded in any non-magnetic material. One example may correspond to the detection of anomalies in magnetically responsive threads interwoven in a cloth material useful, for example, as EMI or RFI shielding for individuals and/or electronic equipment.

Reference will now be made in detail to the presently preferred embodiments of the subject metallic cable anomaly detection method and apparatus. Referring now to the drawings, FIG. 1 illustrates an exemplary configuration of a Hall effect and permanent magnet sensor 100 constructed in accordance with present technology.

As illustrated in FIG. 1, a pair of Hall effect devices HE1, HE2 is mounted in a generally vertical aligned plane with a permanent magnet 102 on an end face 106 of support structure 104. In general it should be appreciated that Hall effect devices HE1, HE2 are mounted along a common line 110 and that measurement aspects related to this location of the Hall sensors are important aspects of the present subject matter as will be addressed throughout the present disclosure. It should be appreciated also that in alternative embodiments, plural pairs of Hall effect devices or an array of such sensors may be employed in association with single or multiple permanent magnets. Further, plural sensors as generally illustrated in FIG. 1 may be employed in a composite configuration. In either instance, opportunity may be provided to examine larger areas and/or multiple cables. It should be further appreciated that, although the present disclosure is directed more specifically to the use of Hall effect sensors, such is not a limitation of the present subject matter at all as other types of magnetic field responsive sensors may also be employed. For example, magneto-resistive sensors may be utilized to substantially equal effect.

In accordance with present technology, for the exemplary embodiment of FIG. 1, at least the end face 106 of support structure 104 corresponds to an insulating surface so as to provide electrical isolation of the Hall effect devices HE1, HE2. Permanent magnet 102 may be secured to a top surface 108 of support structure 104 by any suitable means and is oriented as illustrated in FIG. 1 so as to substantially align, for example, the north pole N of the permanent magnet 102 with the front face 106, and correspondingly with the Hall effect devices HE1, HE2, of the support structure 104. An optional automated control system 120 may be provided to automatically sweep sensor 100 over an area to be examined. It should be appreciated that such a system may be configured to cause relative motion between the sensor and the item being examined so that either or both of the examined item and sensor may be moved by control system 120.

In an exemplary configuration, permanent magnet 102 may correspond to a 12.7 by 25.4 mm Ni—Cu—Ni plated 44-pound pull Neodymium magnet producing 12,900 gauss. Other magnets with similar characteristics may, of course, be used. Further, support structure 104 may correspond to a 75 by 37 by 37 mm aluminum strut with a non-conductive cardboard paper secured to one face while Hall effect devices HE1, HE2 may correspond to 4 mm sq. semiconductor devices spaced approximately 8 mm apart with one edge of Hall effect device HE2 spaced approximately 4 mm from the edge of face 106 opposite from permanent magnet 102. Such positioning of Hall effect devices HE1, HE2 relative to permanent magnet 102 produces a magnetic flux across both Hall effect devices as more particularly shown in FIG. 2. It should be appreciated that, in other embodiments of the present subject matter, an electromagnet may be employed instead of and/or in addition to permanent magnet 102. It should be further appreciated also that different magnet configurations may also be used as well as different orientations of the magnets as well as other configurations of magnets, per se, including without limitation bar magnets, toroidal magnets, cylindrical magnets, horseshoe shaped magnets, and other configurations.

In alternative embodiments, support structure 104 may correspond to any non-ferrous material including without limitation, Plexiglas®, wood, Cycolac® or other plastic materials. Depending on the physical characteristics of the non-ferrous support structure 104, Hall effect devices HE1, HE2 and permanent magnet 102 may be at least partially embedded in the material for support thereof.

Figure 2:
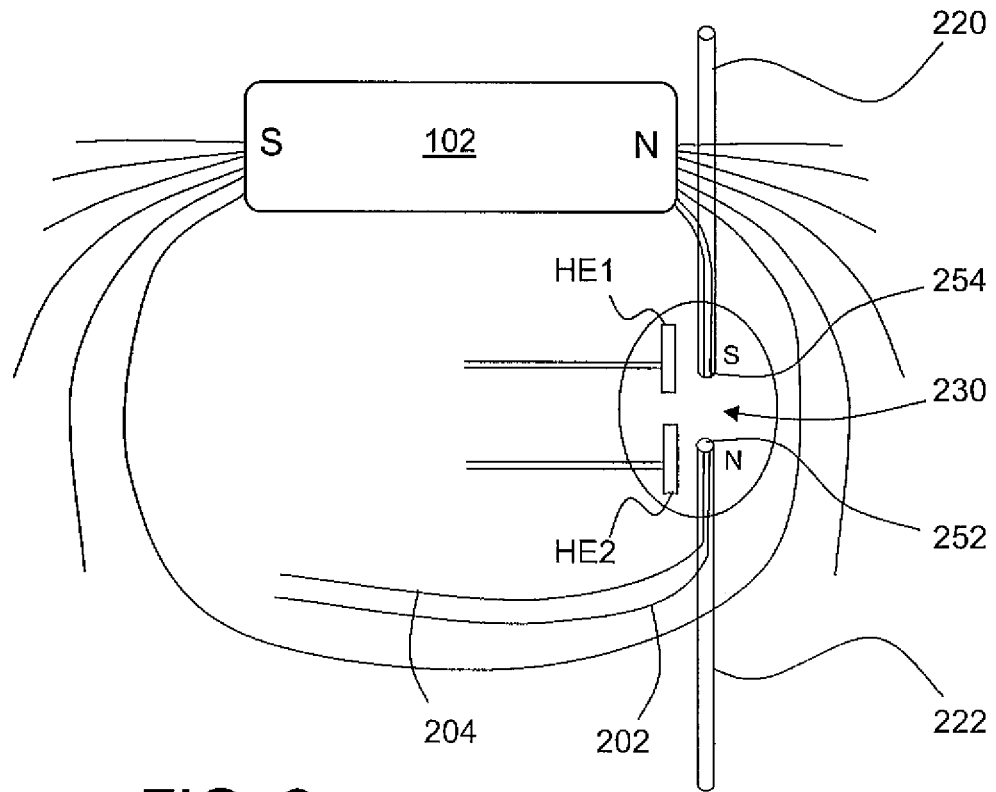
FIG. 2 illustrates relative positioning of a pair of Hall effect sensors to a permanent magnet together with exemplary flux patterns in the presence of a tire cable including an exemplary anomaly.

With reference to FIG. 2, there is illustrated the relative positioning of a pair of relatively closely spaced Hall effect sensors HE1, HE2 relative to a permanent magnet 102 together with exemplary flux lines 202, 204 in the presence of a tire cable 220 including an exemplary anomaly representatively illustrated as a break at 230.

Figure 4:
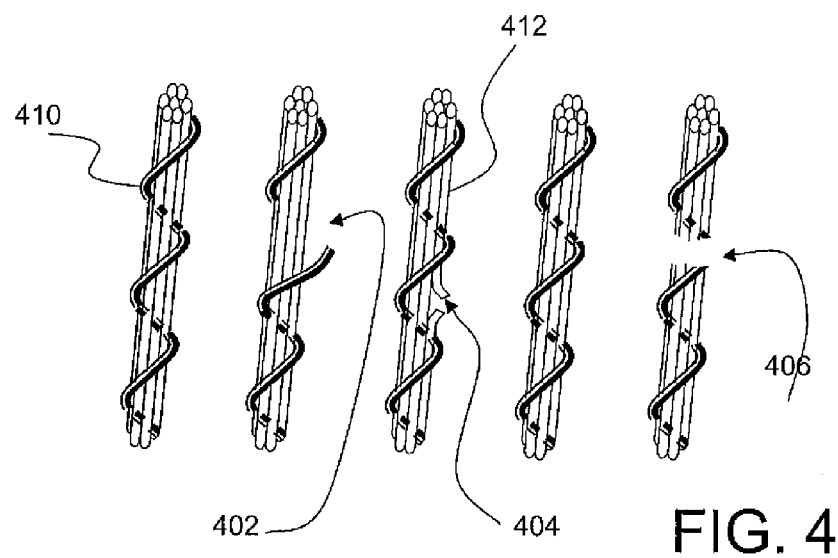
FIG. 4 is a schematic representation of an x-ray view of representative anomalies in a tire cable as may be detected using the present technology.

With brief reference to FIG. 4, it will be seen that FIG. 4 provides a schematic representation of an x-ray view of representative anomalies 402, 404, 406 in tire cables as may be detected using the present technology. As illustrated in FIG. 4, anomaly 402 corresponds to a break in wrapping wire 410, anomaly 404 corresponds to a break in one of the steel strands 412, and anomaly 406 corresponds to a break in the entire cable. Anomalies 402 and 404 are considered to be lesser anomalies while anomaly 406 is considered to be a more significant anomaly.

With further reference now to FIG. 2, as previously noted, an anomaly in the tire cable presently illustrated as break 230 will resulting in a change in the magnetic field presented to Hall effect sensors HE1, HE2. It will be appreciated by those of ordinary skill in the art that the flux lines 202, 204 at least in the area of break 230 proximate to relatively closely spaced Hall effect sensors HE1, HE2 have deviated from a prior path through an unbroken cable and now follow alternate paths through portions 220, 222 of the exemplary broken tire cable. Such a break produces local North and South magnetic poles 252, 254, which alter the magnetic field proximate to relatively closely spaced Hall effect sensors HE1, HE2 to produce at least detectable levels of perpendicular field patterns produced by the anomalies.

It should be appreciated that any of the various anomalies noted above with respect to the discussion of FIG. 4 will produce, to varying degrees, detectable variations in the magnetic field due to the generation of at least some perpendicularly, to the plane of the Hall effect sensors, oriented fields. Within the area proximate Hall effect sensors HE1, HE2, these anomalies may be detected as differences between the signals generated between Hall effect devices HE1, HE2. Outside the area proximate Hall effect sensors HE1, HE2, variations in magnetic fields may also be detected and may be manifested as unidirectional variations in the magnetic field versus a previously detected base magnetic field. It being one of the goals of the present subject matter to identify and locate anomalies, however, the present subject matter is more directly related to and described in association with the detection of magnetic field differences detectable between Hall effect sensors HE1, HE2.

Other analysis of Hall effect signals may be made, however, of unidirectional variations in magnetic fields. It should be appreciated that, with respect to the present discussion, the term difference is not meant to describe only a mathematical subtraction of one signal from another, but rather to broadly include various forms of analysis that seek to analyze identifiable differences between signals generated by at least one pair of sensors, as will be explained more fully with respect to the various embodiments of the subject matter herein presented.

Figure 3:
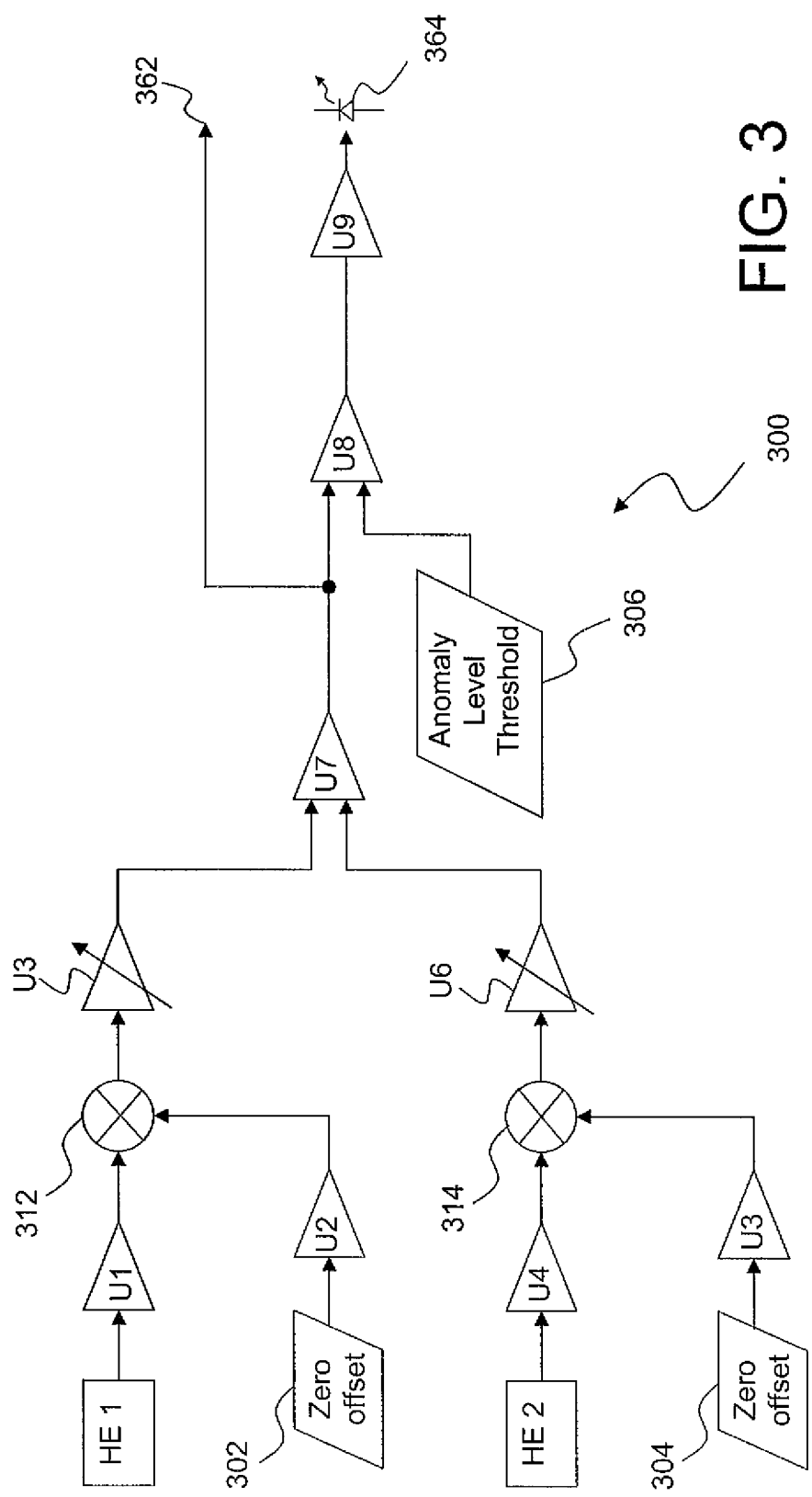
FIG. 3 illustrates a block diagram of an exemplary signal processing circuit configured to process signals from a pair of Hall effect devices to provide an indication of the presence of tire cable anomalies.

With reference now to FIG. 3, there is illustrated a block diagram of an exemplary signal processing circuit 300 configured to process signals from a pair of Hall effect devices HE1, HE2 and to provide an indication of the presence of tire cable anomalies. As may be seen, signal-processing circuit 300 receives signals from Hall effect sensors HE1, HE2 by way of non-inverting followers or buffers U1, U4, respectively.

In an exemplary configuration, followers U1, U4, as well as the other amplifiers within signal processing circuit 300, may correspond to LM741 CN operational amplifiers, Of course other suitable forms of these operational amplifiers, as for example, devices containing a plurality of equivalent amplifiers or other similar devices may be employed. Those of ordinary skill in the art will appreciate that the terms follower and buffer are synonymous terms and are used as such throughout the present disclosure. Further, in this exemplary configuration, Hall effect devices HE1, HE2 may correspond to A1302 ratiometric linear Hall effect sensors available from Allegro Microsystems, Inc. Again, similar type devices may be employed as well as different type devices.

With further reference to FIG. 3, it will be seen that there is associated with each Hall effect device's HE1, HE2 input circuit, buffer amplifiers U1, U4, respectively, which provide buffered signals to one input each of mixers 312, 314, respectively. Amplifiers U2, U5, respectively, provide buffered zero offset signals from zero offset circuits 302, 304, respectively, to sum, via second inputs to mixers 312, 314, respectively, with respective signals from Hall effect devices HE1, HE2 to offset the Hall effect devices' outputs. Output signals from mixers 312, 314, respectively, are provided as inputs to variable gain adjustable buffer amplifiers U3, U6. Amplifiers U3, U6 are configured as gain adjustable devices so as to develop desired overall signal gain and corresponding sensitivity. Amplifiers U3, U6 may also be configured to provide low-pass filtering as necessary.

In an exemplary configuration, zero offset circuits 302, 304 may correspond to adjustable potentiometers tied to appropriate voltage sources and coupled to the non-inverting inputs of buffers U2, U5, respectively. In other configurations, zero offset signals may be provided as digital inputs for microprocessor enabled embodiments or for digital to analog converter enabled embodiments. Still other embodiments of the present subject matter may incorporate automated zero averaging of each of the Hall effect sensor signals.

When Hall effect devices HE1, HE2 are introduced into a magnetic field that is perpendicular to the Hall device sensor plane, the output of the device will be proportional to the applied and sensed magnetic field strength within the specific linear range of the device. Amplifier U7 receives the offset adjusted and buffered signals from each of the Hall effect devices HE1, HE2 and amplifies any difference between the two signals. In this particular embodiment of the present subject matter, the difference between the two signals is evaluated based on a mathematical subtraction of the two signals. As previously noted, in other embodiments, as will be explained further later, alternative difference analysis of the signals may be provided. In an exemplary configuration of the embodiment of FIG. 3, amplifier U7 is configured as a 10× fixed gain amplifier although in other embodiments different fixed gain levels may be provided or, alternatively yet, amplifier U7 may be provided as an adjustable gain amplifier similar to amplifiers U3 and U6.

An output signal from amplifier U7 may be provided at terminal 362 for monitoring by an appropriate device such as, for example, a voltage measuring or displaying device as a voltmeter or oscilloscope (not illustrated) and may also be applied as one input to comparator U8.

Comparator U8 may be provided, for example, by configuring an operational amplifier as an open loop amplifier and is used as a threshold detector that switches output levels when the output of amplifier U7, that is provided to one input of comparator U8, exceeds a reference level signal applied from anomaly level threshold adjustment circuit 306. The output signal from comparator U8 is sensed by buffer/driver U9 to illuminate a visually observable indicator, for example, a light emitting diode (LED) 364 for visual confirmation of a detected anomaly such as a broken sidewall wire or other anomalies as previously discussed herein above.

Those of ordinary skill in the art should also appreciate that various levels of detection can be achieved through variations in the gain settings of amplifiers U3 and U6 as well as by adjustment of anomaly level threshold adjustment circuit 306. Further, those of ordinary skill in the art will appreciate that the signal applied from anomaly level threshold adjustment circuit 306 may be provided in a manner similar to that of the signals from zero offset circuits 302, 304 and may correspond to voltage signals from adjustable potentiometers with appropriate input voltages or from digital input signals as previously discussed herein above depending on the apparatus implementation selected. In certain embodiments, anomaly level threshold adjustment circuit 306 may be manually adjusted either by manual setting of a voltage level adjusting potentiometer or by manual entry of appropriate data for a digital implementation.

The device so far discussed with reference to FIGS. 1-3 and especially structurally with respect to FIGS. 1-2 may be configured in multiple embodiments depending on desired physical operational desires. For example, the device illustrated generally in FIG. 1 may be affixed to a further support structure so as to implement an automated examination of a tire structure. In such a configuration, an automated control system 120 generally illustrated in phantom in FIG. 1, may be employed to automatically sweep the sensor across tire areas, for example the inner surface of the area of a tire to be examined. Alternatively, other methodologies for providing relative motion between the sensor and tire may also be implemented including enabling automated control system 120 to move either or both of the sensor and tire. Of course the sensor may also be configured as a compact portable handheld device that may be manually swept across either inner or outer areas of a tire to be examined.

In accordance with further features of the present subject matter, a sensor as illustrated in FIGS. 1-2 may be mounted on a machine configured to rotate a tire or the sensor assembly to position the sensor assembly in a radial fashion on the inside surface of the tire carcass thereby effectively presenting the entire inside surface of the tire carcass to the sensor for cable evaluation. The sensor may be coupled to a personal computer (PC) or animation system to provide positional feedback allowing for precise information of the sensor assembly location in relation to the tire surface whereby localization, size, including number of cables involved, and severity of anomalies can be presented to an operator. Further, as will we explained more fully later, the PC may also be used to implement alternative evaluation methodologies.

A system of signal conditioning similar to that described in association with FIG. 3 and an associated analysis algorithm may be provided to produce diagnostic information on the condition of the subject tire in multiple forms. Such forms may include a topographical representation of magnetic structures within the tire. The size and shape of three dimensional (3-D) magnetic responses may be evaluated to detect and measure anomalies that include, but are not limited to: broken reinforcement cables; reinforcement cables with one or more broken wires; bent reinforcement cables; corroded reinforcement cables; and metallic objects penetrating the reinforcement wire plane. Presentations may including a colored surface representation of the magnetic structures in the tire as well as analysis of isocontour nodes to the operator allows detection and measurement of anomalies as previously noted. Such a system could also be configured to provide a numeric table of anomalies, indicating the location, size, shape and intensity of the magnetic anomalies in the tire while analysis of the numeric data would allow detection and measurement of anomalies as previously noted.

In a handheld configuration, the technology in accordance with the present subject matter may conveniently provide a visual indicator such as LED 364 (FIG. 3) to provide immediate indication of an anomaly to an operator. Further a manual adjustment of the anomaly level threshold circuit 306 (FIG. 3) may be provided for operator convenience in adjusting the sensitivity of a handheld embodiment.

Because of the arrangement of the permanent magnets 102 and Hall effect sensors HE1, HE2 the embodiment of the present subject matter illustrated in FIGS. 1 and 2 is well suited for use in a compact portable handheld configuration, although such is not a limitation of the present technology as such a configuration may also be used in an automated configuration as described previously. In either instance, it has been found that it is advantageous for best detection results to maintain the common line on which the sensors are mounted generally parallel to the tire cables. Such positioning provides maximum signal detection capability for the present subject matter although absolute parallel orientation is not required for anomaly detection.

In accordance with present technology as mentioned above, signal processing may be accomplished using different methods. As previously discussed with reference to FIG. 3, certain of the methods may not require the use of any computer processing. In such embodiments, signal processing may be carried out using a custom circuit board as previously exemplarily illustrated in FIG. 3. That method amplifies and subtracts the signals from HE1 and HE2 to produce a difference signal which is amplified and compared to a threshold voltage to illuminate a light emitting diode (LED) if an anomaly is located as previously discussed. It should, of course, be appreciated by those of ordinary skill in the art that while this previously described method may be performed using the circuitry illustrated in FIG. 5, other circuitry including without limitation, personal computers and application specific programmable device may also be used to perform the same signal processing as described with respect to FIG. 3, or alternate signal processing as described below.

Figure 5:
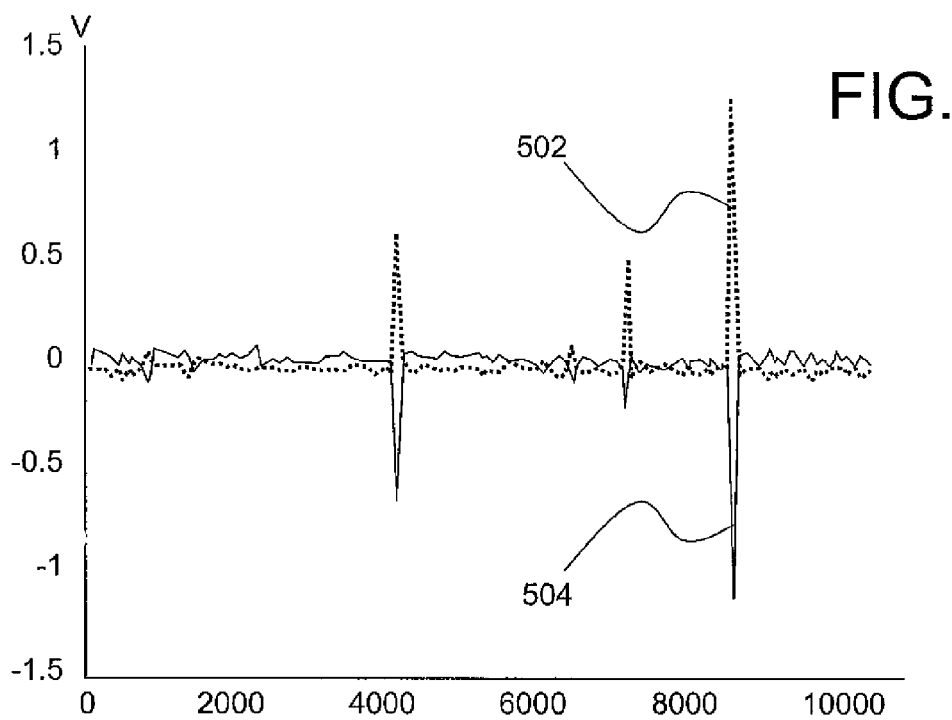
FIG. 5 graphically illustrates filtered and averaged data collected during an automated sweep examination of a tire in accordance with present technology.
Figure 6:
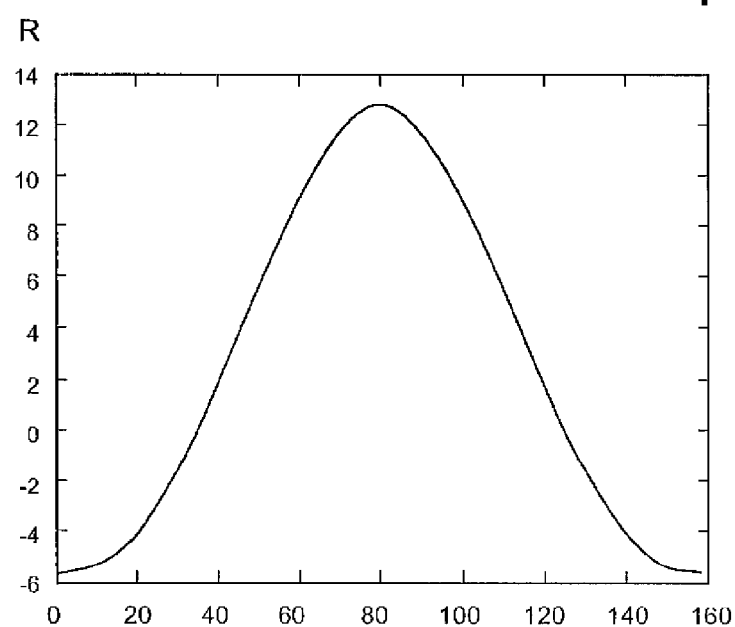
FIG. 6 graphically illustrates a exemplary convolution operator as may be employed in an alternative data analysis methodology.

In accordance with further embodiments of the present technology, alternative signal processing may be employed as will be discussed with reference to FIGS. 5 and 6. With reference to FIG. 5, sensors constructed in accordance with the present technology may be swept across a tire using an automated control system 120 as representatively illustrated in FIG. 1. Collected data may be stored temporarily or more permanently for post processing using a number of different methodologies but each employing analysis methods that examine signals from one or more pairs or an array of sensors that look for identifiable differences in the signals.

In an exemplary embodiment, Matlab® signal processing software available from The MathWorks™ may be employed to analyze the collected data. In an exemplary configuration, a data collection system configured to examine the sidewall of a tire may contain approximately 40,000 points per data track of the sidewall. Of course, this points per track is exemplary as alternative numbers of samples may be collected. It should be noted here that the points per track represents a single pass or tracks around the tire sidewall. A significant feature of the present technology is that it may be used to good advantage with such a single pass, or a small number of passes, to locate the azimuth of an anomaly while not the precise radial position on the tire.

The purpose here is to determine in one or two rotations of the tire if any cable is broken. It is intended to provide the azimuth of the broken cable and possibly which side of the tire. The principle is that most tires scanned will not have a broken cable. If one is found, a more time consuming automatic sweeping or manual handheld method could be employed to accurately locate the anomaly. In more general embodiments of the present technology, plural passes will be used to exactly locate anomalies both by azimuth and radial location.

A first step in evaluating collected data is to resample and filter the data points collected from Hall effect sensors HE1 and HE2. An encoder may be employed to provide, for example, approximately 10,800 pulses per revolution of the tire. It will be appreciated by those of ordinary skill in the art that this exemplary sample size will change based on tire dimension and rim size. The resample routine averages the data points of each Hall Effect signal for the same encoder points to one encoder point. This results in a waveform for each sensor of 10,800 points around the circumference of the tire. After the data has been re-sampled, a $5^{th}$ order Butterworth filter is applied. In an exemplary configuration, the cutoff frequency of the filter may be set to 0.025. In any event, this cutoff frequency value must be set between 0 and 1 and represents a proportional frequency of the raw data frequency content. The result of this step is re-sampled and filtered waveforms 502, 504 that may be displayed as illustrated in FIG. 5.

As represented in FIG. 5, waveform 502 corresponds to a re-sampled and filtered signal from sensor HE1, while waveform 504 corresponds to a similar signal from sensor HE2. It will be noted that the opposite direction spikes occur simultaneously as the sensors react to anomalies within the tire. Lesser anomalies are displayed as lesser amplitude signals while more significant anomalies are identified by larger amplitude signals. As illustrated in FIG. 5, signals represented by waveforms 502, 504 may be measured in terms of volts (V) in the vertical axis while samples numbers are shown along the horizontal axis.

Following re-sampling and filtering, both sensor signals are simultaneously processed using a sliding window. In this window, the slope of each sensor signal is calculated and compared to each other and to a threshold value. If the slopes are opposite to each other and if each slope is greater than the threshold value, an output slope magnitude waveform representing the combined slope magnitude is produced.

The slope magnitude waveform may then be processed by searching the waveform point by point to determine the presence of a signature signal identified by a positive slope followed relatively quickly by a negative slope. The time difference between the detection of a positive and negative slope each exceeding a predetermined threshold may be based on a known anomaly size. If such a signature is encountered, an output waveform is produced from the combined sensor HE1 and sensor HE2 magnitudes. This results in a waveform with positive spikes representing the combined amplitude of sensor HE1's negative spike and sensor HE2's positive spike. The resulting waveform can be visually inspected and, if desired, a table of values may also be produced that can be inspected in terms of magnitude and spike width.

In an alternative analysis methodology, a convolution approach may be used. The convolution involves several steps as follows. First a convolution operator as illustrated in exemplary form in FIG. 6 is selected. This shape has been selected for its match to less than full cable anomalies. In an exemplary configuration, the operator is based on a so-called Mexican Hat wavelet or, more commonly, a Ricker wavelet, and in an exemplary configuration is 160 points wide with a sigma of 45. In mathematics and numerical analysis, the Mexican hat wavelet is the negative normalized second derivative of a Gaussian function and is a special case of the family of continuous wavelets known as Hermitian wavelets. In the exemplary configuration illustrated in FIG. 6, relative values R are indicated along the vertical axis while sample points range from 0 to 160 as previously noted. An exemplary convolution operator in accordance with present technology is based on a relationship where the sum of the values R over the sample range is equal to zero.

Following development of the convolution operator, signals from sensor HE1 and HE2 are averaged to zero. Such averaging to zero entails taking the average of each waveform and then subtracting the average from each sensor waveform. The operator is applied to each waveform and the resulting two waveforms are multiplied together.

Several heuristics are then applied. First, eliminate operator matches for sensors HE1 and HE2 that are in the same direction, i.e., both positive or both negative. This heuristic is applied as both theory and experimental experience indicates that an anomaly will cause the sensor signals to deflect opposite from each other.

Second, because the Mexican Hat operator causes 'brims' to result around a positive response, these responses should be eliminated from consideration. Third, only retain responses where sensor HE2 is positive and sensor HE1 is negative. This is applied because theory and experience indicates that with proper magnet pole orientation, one sensor will always provide a positive response and the other negative.

After the above convolution steps are applied, a resulting waveform is created. This resulting waveform can be visually inspected and a table of values may also be produced that can be inspected in terms of magnitude and spike width. This resulting waveform represents a degree of match to the operator and is proportional to the amplitude and shape of an anomaly.

Figure 14:
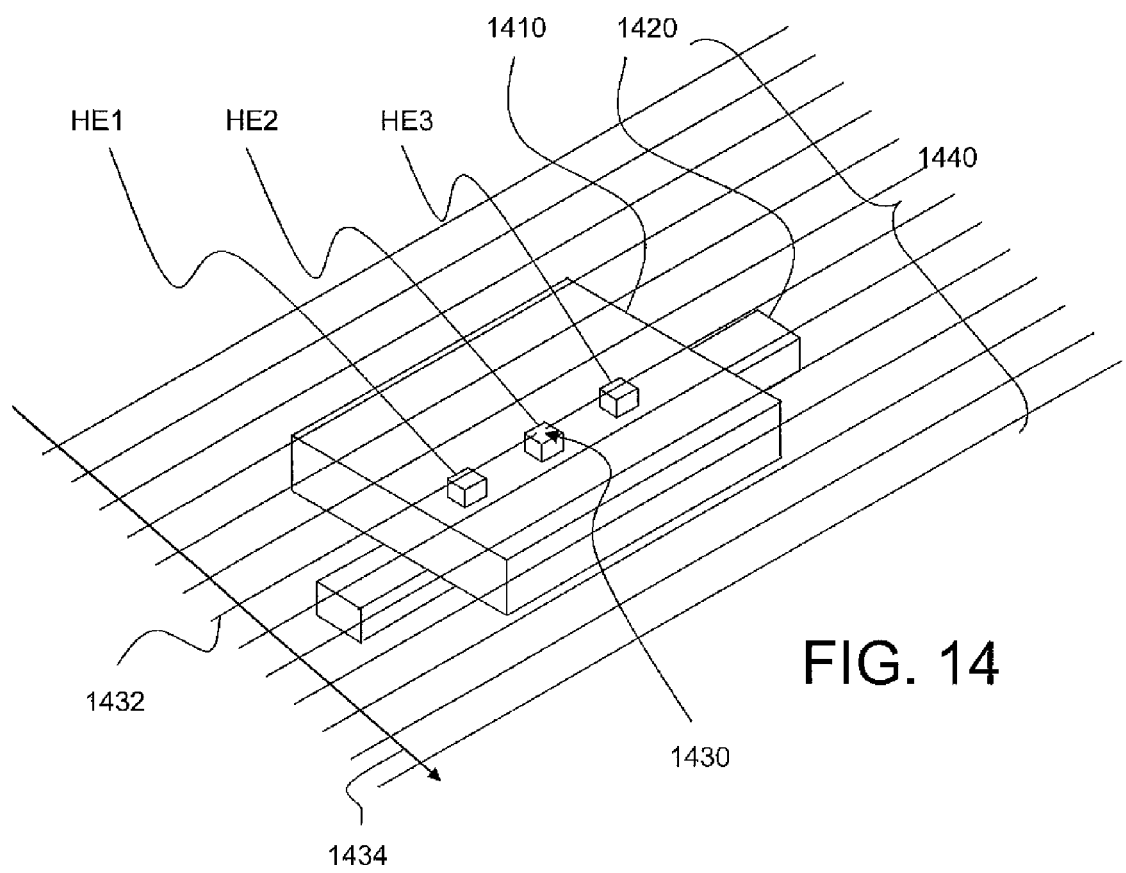
FIG. 14 illustrates a configuration of a sensor array useful in explaining the advantages of the present technology.

With reference first to FIG. 14, there is illustrated another embodiment of a sensor assembly on which the present technology is based corresponding to a sensor array including three sensors HE1, HE2, HE3 mounted along a common line and configured to produce separate output signals. In an exemplary configuration sensors HE1, HE2, HE3 are surface mount chip type Hall effect devices and are mounted on a common substrate (not separately illustrated) affixed to circuit board 1410. It should be appreciated, however, that other types of sensors may be used. A permanent magnet 1420 is associated with printed circuit board 1410 and sensors HE1, HE2, HE3 and is positioned so that the north and south poles of the permanent magnet are aligned with the common line on which the sensors HE1, HE2, HE3 are mounted. In an exemplary configuration, magnet 1420 may correspond to a pair of ¼" by ¼" by 1" N50 neodymium magnets placed end to end with complimentary poles in effect creating one 2" long magnet.

In the embodiment shown in FIG. 14, sensors HE1 and HE2 are considered as a first pair while sensors HE2 and HE3 are considered as a second pair. This configuration enables doubling the surface area covered in a single pass of the sensor assembly to reduce the total testing cycle time. In so doing, the signal processing is handled in a manner similar to previously discussed embodiments with reference to FIG. 3 in that fixed pairing of sensors are maintained while scanning for damaged tire cables including, for example, break 1430 in cable 1432 while the sensor and magnet assembly scanned generally in the direction of arrow 1434 over the multiple cables collectively illustrated as cables 1440.

It has been found, however, that the use of more than two pairs of sensors results in further enhancements well beyond simply speeding up testing cycle time if all combinations of sensors provided are considered. In the case of the configuration of FIG. 12 then, in addition to considering HE1 and HE2 as a pair and HE2 and HE3 as a pair, one may also consider HE1 and HE3 to be a pair. In this instance, with substantially equal spacing among each of the three sensors, additional information may be derived based on the increased spacing between the pair corresponding to HE1 and HE3.

Further still, with reduced spacing between the sensors made possible by using smaller devices such as, but not exclusively, surface mounted chip type sensors coupled with the provision of an increased number of sensors beyond the three illustrated in FIG. 14, further advantages are obtained that allow for not only an improvement in testing cycle time but also improved ability to detect anomalies in the tire cables.

Figure 7:
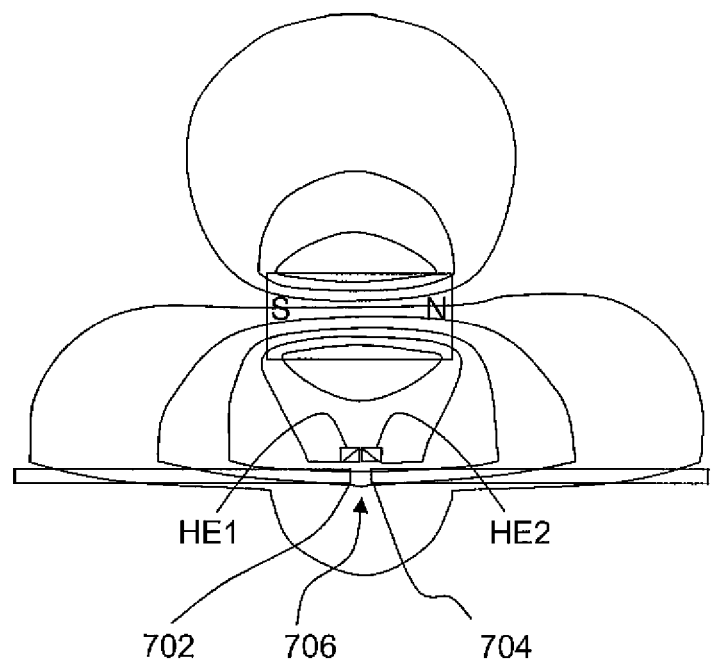
FIG. 7 illustrates flux lines resulting from spacing the sensors such that sensor centers are centered directly over each end of a single complete tire cable break.
Figure 8:
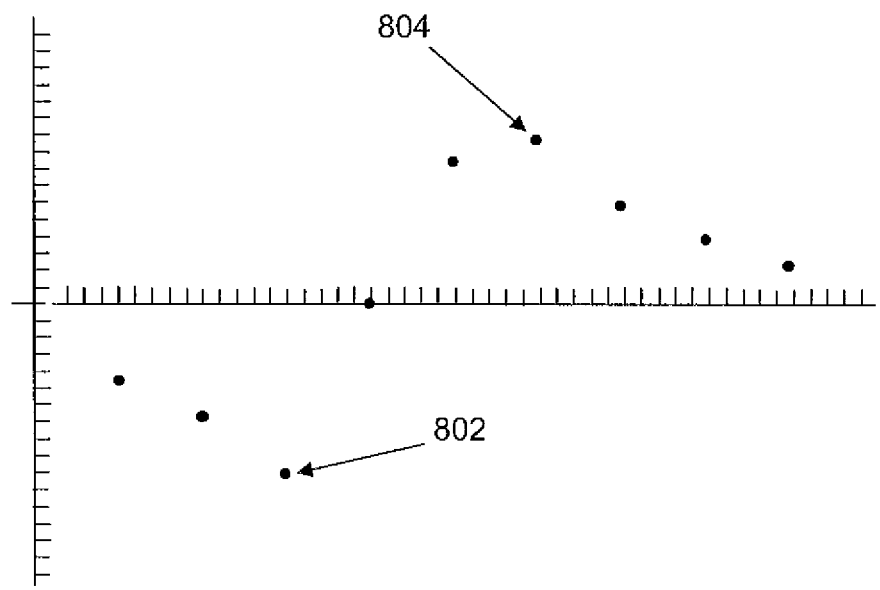
FIG. 8 illustrates a plot of flux magnitude and highlights by illustrated arrows of readings when the centers of the sensors are placed over each end of a single complete tire cable break.

With reference now to FIGS. 7-8 a further understanding of the principles underlying the present technology may better be obtained. As a preliminary matter, it has been appreciated that by employing a sensor configuration as illustrated in FIG. 14 where only the pairs HE1, HE2 and HE2, HE3 are considered, three problems may occur. A first problem may occur when one sensor is lined up with an area of cable damage. A second problem may occur in the instance of low-level damage providing very low flux leakage that may not be readily detected by the sensors due to proximity of maximum leakage to a sensor. Thirdly, cable separation may be greater than the spacing between sensors.

To be able to understand how to address the problems mentioned above, it is necessary to identify the ideal relationship between sensor arrangement and cable damage. A single complete cable break will be used for illustration; however, the concept can be extended to sub-cable damage very readily. It has already been established that a pair of sensors will provide a self-referencing system where damage is detected by positive flux detection on one sensor with negative flux detection on the other sensor. The ideal location for the damage is centered between the magnet ends with the sensors located directly over the ends of the damage as illustrated below. The resultant damage magnitude detection is, in the end, the sum of the absolute value from each sensor; therefore, it is ideal that each sensor be placed in a manner to sense the maximum flux leakage from the damage.

With reference to FIGS. 7 and 8, there are illustrated in FIG. 7 flux lines produced from a permanent magnet resulting from spacing a pair of sensors HE1, HE2 such that the sensor centers are centered directly over each end 702, 704 of a single complete tire cable break 706. FIG. 8 illustrates a plot of flux magnitude, highlighting by illustrated arrows 802, 804, exemplary readings when the centers of the sensors are placed over each end 702, 704 of single complete tire cable break 706. As can be seen from the plot of FIG. 8 at arrows 802, 804, the maximum flux leakage is centered directly over each end 702, 704 of the damage.

Figure 9:
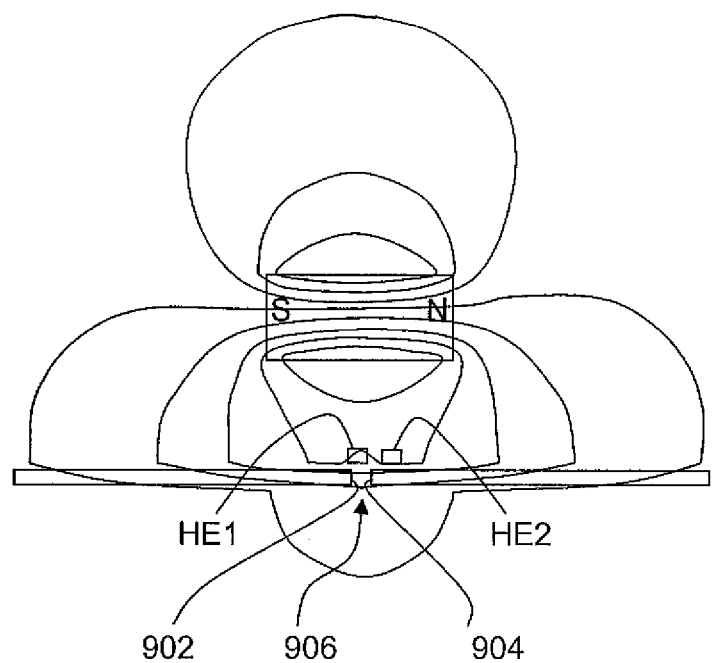
FIG. 9 illustrates flux lines resulting from spacing the sensors with an exemplary 10 mm center to center spacing where one sensor is aligned with one end of a single complete tire cable break.
Figure 10:
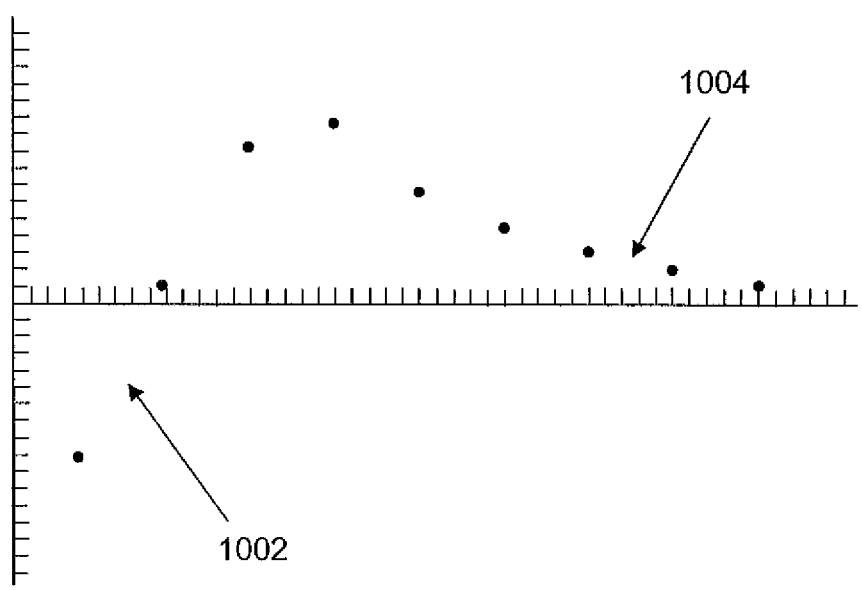
FIG. 10 illustrates a plot of flux magnitude and highlights by illustrated arrows of readings when the centers of the sensors are positioned as illustrated in FIG. 9.

FIGS. 9 and 10 illustrate the first problem identified above, i.e., that of one sensor HE1 being lined up with an area of cable damage 906 as opposed to over one of the cable break ends 902, 904. In this instance as may be seen from the flux magnitude plot of FIG. 10, where arrows 1002 and 1004, respectively, indicate the flux magnitude at the center of each sensor HE1, HE2 as located as illustrated in FIG. 9, neither sensor will detect the full leakage available due to being positioned off center from the optimum placement over the ends of the damage as previously illustrated in FIG. 7.

The second problem identified above, that of low level damage detection where the edges of the damage are closer together than the spacing between sensors relates, at least in part, to the center to center spacing of the sensors. In an exemplary configuration, center-to-center spacing was set at 10 mm. In such instance, smaller damages are likely to pass off center and far away from the optimum location for each sensor. While the damage may be close enough to one sensor to provide the appropriate flux leakage indication, it is possible for the other sensor to be so far away from the edge of the damage that it will have no indication of flux leakage. With the exemplary 10 mm spacing noted, the spacing would be optimal only if the damage was 10 mm in width.

Figure 11:
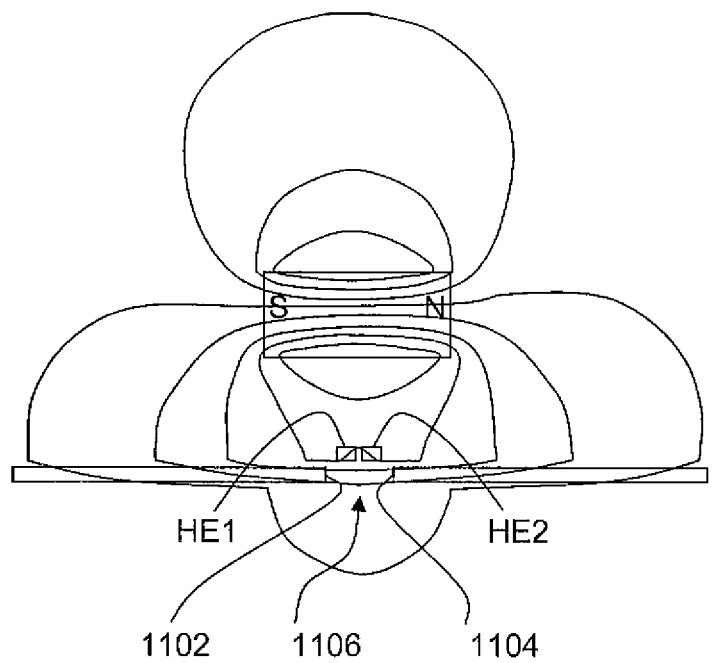
FIG. 11 illustrates flux lines resulting from damage separation greater than the sensor spacing.
Figure 12:
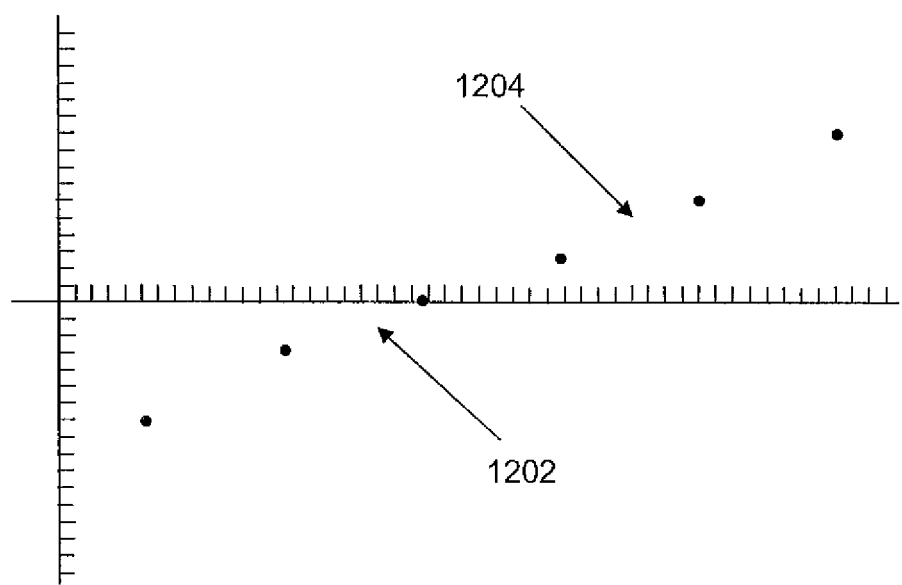
FIG. 12 illustrates a plot of flux magnitude and highlights by illustrated arrows of readings when the centers of the sensors are positioned as illustrated in FIG. 11.

Referring now to FIGS. 11 and 12 the effects of the third problem identified above, i.e., that of anomaly separation greater than the sensor spacing are illustrated. If the damage separation is greater than the center-to-center distance of the sensors HE1, HE2, the maximum flux leakage cannot be detected because the sensors will not be located at the edge 1102, 1104 of the damage 1106. As illustrated in FIG. 12 by arrows 1202 and 1204 the flux leakage sensed at the center of each sensor HE1, HE2 as shown in FIG. 11 is not the maximum flux leakage, thus such maximum flux leakage will not be sensed in this configuration.

In order to address these problems the present technology provides for two variations of the previous embodiments that together operate synergistically to provide improved anomaly detection.

If one were to address only the first problem, i.e., that of a sensor pair lining up incorrectly with the maximum flux leakage, such might be addressed by decreasing the spacing between subsequent scans of the tire to increase the likelihood that the damage will fall between the sensor pair rather than offset from it. Such a solution, however, would have the undesirable effect of increasing the cycle time for a complete scan of the tire and, of course, does not address the second and third problems at all.

In accordance with present technology, all three identified problems are address by way of the combination of modifications to the sensor assembly along with a modification of the methodology for analyzing the sensor output signals. An exemplary structural modification of the sensor may be seen with reference to FIG. 13 while the modification to the signal analysis methodology may be more clearly understood with reference to Table 1 herein below. The physical modification involves densely packaging as many sensors as possible or practical into the same footprint previously used.

Figure 13:
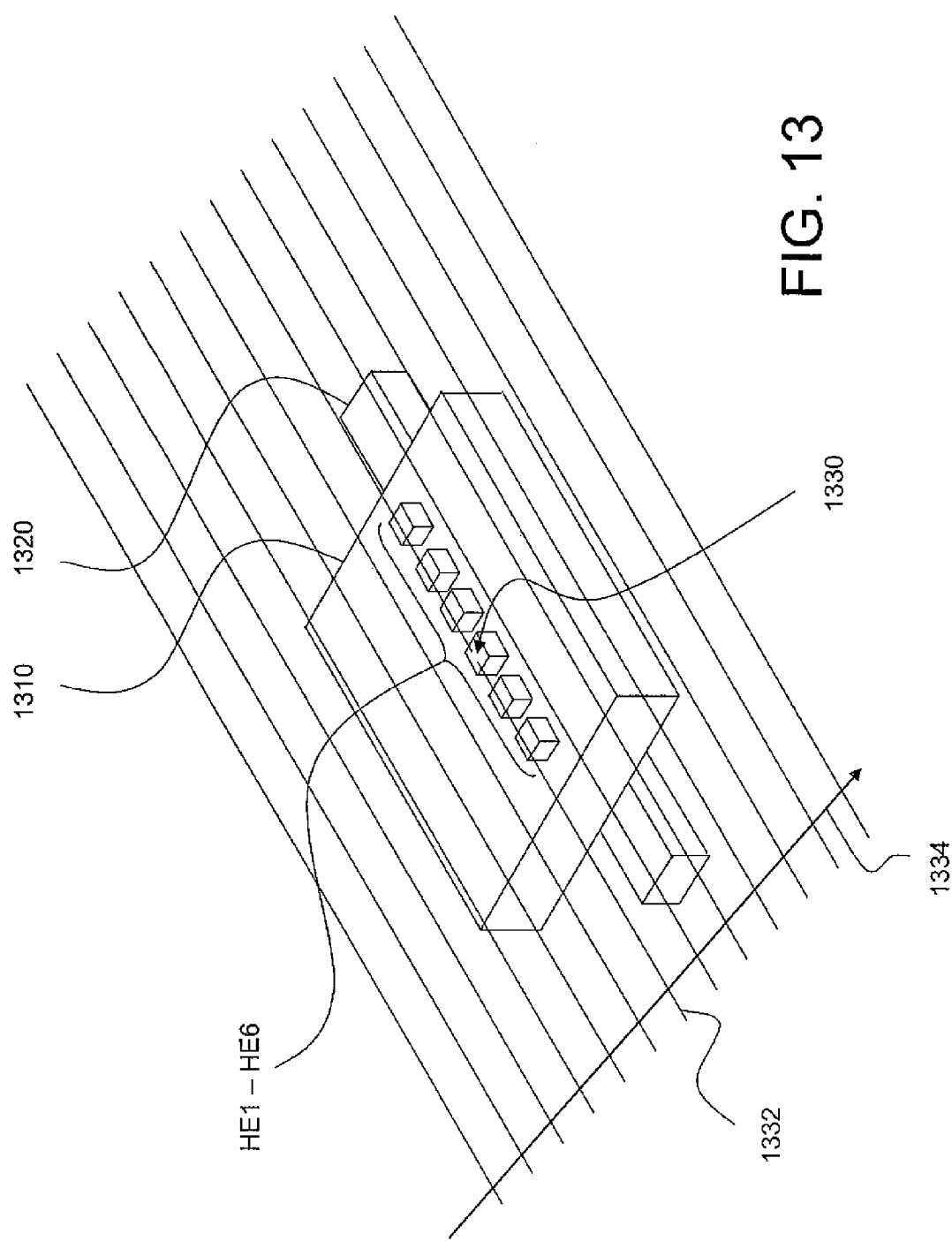
FIG. 13 illustrates an exemplary sensor array in accordance with present technology operatively positioned with respect to exemplarily illustrated tire cables.

In an exemplary configuration as shown in FIG. 13 in positional relationship to tire cables to be tested, six surface mount chip type magnetic sensors HE1-HE6 are placed along a common line on a printed circuit board 1310. In an exemplary configuration the six surface mount chip type magnetic sensors HE1-HE6 may be positioned on a 4 mm center to center spacing resulting in an overall length for the array of about 20 mm. Magnet 1320 is associated with the sensor array by being placed along the same common line on which the sensors HE1-HE6 are placed in a manner similar to that previously described with reference to FIG. 14. In an exemplary configuration, the chip type magnetic sensors HE1-HE6 and magnet 1320 may correspond to magnet 1420 as described with relation to FIG. 14.

It should be noted that other spacing between sensors is possible as well as other sensor array configurations that effectively reduce the spacing between the sensors. For example, a second physically identical six-sensor array may be place in parallel with the first array and positioned such that the space between sensors in the second array falls between the space between sensors in the first array. Such positioning with appropriate adjustments to the signal processing system would effectively cut in half the spacing between sensors. This concept, of course, could be extended to a third, fourth, etc. parallel sensor array.

As previously noted simple reduction in spacing between magnetic sensors HE1-HE6 only address the first problem identified. In accordance with present technology the other problems identified are addressed via the addition of modifications to the signal analysis methodology wherein each sensor HE1-HE6 in the exemplary configuration of FIG. 13 is paired with every other sensor in the array. Under such an arrangement, a six sensor array of sensors HE1, HE2, HE3, HE4, HE5, and HE6 provides fifteen pairs of sensors

TABLE 1

| | |
|---|---|
| HE1 | HE2 |
| HE1 | HE3 |
| HE1 | HE4 |
| HE1 | HE5 |
| HE1 | HE6 |
| HE2 | HE3 |
| HE2 | HE4 |
| HE2 | HE5 |
| HE2 | HE6 |
| HE3 | HE4 |
| HE3 | HE5 |
| HE3 | HE6 |
| HE4 | HE5 |
| HE4 | HE6 |
| HE5 | HE6 |

In accordance with present technology, each sensors' output signal magnitude is evaluated and the strongest positive flux leakage detection signal is paired with the strongest opposing, i.e., negative, flux leakage detection signal to provide the "pair" that produces a resultant damage magnitude signal to the exclusion of the remaining signals for that particular portion, i.e., azimuth of the tire. In other words, the highest positive signal is paired with the highest negative signal and the remaining signals are ignored. By way of example and with reference to FIG. 5, signals similar to the positive going signal at 502 and the negative going signal at 504 would be selected to be paired while the lesser illustrated signals would be ignored. By employing this apparatus configuration and analysis methodology, all the problems previously addressed will be taken into consideration and will provide a higher likelihood of a sensor passing close to the maximum flux leakage of a damaged cable and allowing the signal analysis methodology to selectively determine which sensor has provided the signal.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An apparatus for detecting tire metallic cable anomalies, comprising:
   a support structure;
   a plurality of magnetic field sensors positioned on the support structure along a common line extending along the support structure and configured to produce individual electrical signals proportional to a sensed magnetic field, each of the individual electrical signals produced by each of the plurality of magnetic field sensors resulting from one of the tire metallic cable anomalies;
   a magnet on the support structure, the magnet having north and south poles thereof positioned to provide a magnetic field at each said plurality of magnetic field sensors parallel to said common line; and
   a signal processing circuit configured to produce signals indicative of differences between pairs of said individual electrical signals from different magnetic field sensors resulting from the one of the tire metallic cable anomalies,
   wherein the electrical signal from each of said plurality of magnetic field sensors is paired with an electrical signal from each of the others of said plurality of magnetic field sensors.

2. The apparatus of claim 1, wherein said plurality of magnetic field sensors comprise surface mount Hall effect sensors.

3. The apparatus of claim 1, wherein said signal processing circuit is configured to pair the strongest electrical signal with the strongest opposing electrical signal to produce a damage magnitude signal while ignoring the remaining electrical signals.

4. The apparatus of claim 1, wherein said signal processing circuit is configured to produce a signal based on one of subtractive signal differences, the presence of opposite sloped signals with slopes each exceeding a predetermined magnitude, and convolution analysis of zero averaged multiplied waveforms.

5. The apparatus of claim 1, further comprising:
   an automated control system configured to automatically present said plurality of magnetic field sensors to a metallic cable for detection of anomalies therein.

6. The apparatus of claim 1, wherein said plurality of magnetic field sensors comprises at least three magnetic field sensors.

7. The apparatus of claim 1, wherein the magnet is a permanent magnet.

8. A method for detecting anomalies in a tire metallic cable, comprising:
   positioning a plurality of magnetic field sensors on a support structure on a common line extending along the support structure;
   positioning a magnet on the support structure, the magnet having north and south poles thereof to provide a magnetic field at each of said plurality of magnetic field sensors parallel to said common line;
   presenting said plurality of magnetic field sensors to a metallic cable; and
   detecting a difference between signals from different magnetic field sensors and resulting from one of the anomalies;
   wherein the electrical signal from each of said plurality of magnetic field sensors is paired with an electrical signal from each of the others of said plurality of magnetic.

9. The method of claim 8, further comprising:
   pairing the strongest positive signal from each of the plurality of magnetic field sensors with the strongest negative signal from each one of the other magnetic field sensors; and
   analyzing the difference between the strongest positive and strongest negative signals to the exclusion of the remaining magnetic field sensor signals.

10. The method of claim 8, wherein detecting a difference between signals comprises producing a signal based on one of subtractive signal differences, the presence of opposite sloped signals with slopes each exceeding a predetermined magnitude, and convolution analysis of zero averaged multiplied waveforms.

11. The method of claim 8, wherein positioning magnetic field sensors comprises positioning surface mount Hall effect sensors.

12. The method of claim 8, wherein positioning a magnet comprises positioning both the north and south poles of a magnet along a line parallel to said common line.

13. The method of claim 8, wherein positioning a plurality of magnetic field sensors comprises positioning at least three magnetic field sensors.

14. The method of claim 8, wherein positioning a magnet comprises positioning a permanent magnet.

* * * * *